United States Patent
Nevins et al.

(10) Patent No.: US 10,531,959 B2
(45) Date of Patent: Jan. 14, 2020

(54) MODULAR, PLASTIC KNEE REPLACEMENT WITH LOCKING MECHANISM

(71) Applicants: Russell Nevins, Las Vegas, NV (US); David Backstein, Toronto (CA)

(72) Inventors: Russell Nevins, Las Vegas, NV (US); David Backstein, Toronto (CA)

( * ) Notice: Subject to any disclaimer, the term of this patent is extended or adjusted under 35 U.S.C. 154(b) by 0 days.

(21) Appl. No.: 16/368,337

(22) Filed: Mar. 28, 2019

(65) Prior Publication Data

US 2019/0298532 A1    Oct. 3, 2019

Related U.S. Application Data

(63) Continuation-in-part of application No. 15/938,986, filed on Mar. 28, 2018.

(51) Int. Cl.
*A61F 2/38* (2006.01)
*A61F 2/46* (2006.01)
*A61F 2/30* (2006.01)

(52) U.S. Cl.
CPC ............ *A61F 2/389* (2013.01); *A61F 2/3859* (2013.01); *A61F 2/4684* (2013.01); *A61F 2002/3038* (2013.01); *A61F 2002/30331* (2013.01); *A61F 2002/30354* (2013.01); *A61F 2002/30403* (2013.01); *A61F 2002/30614* (2013.01); *A61F 2002/30616* (2013.01); *A61F 2002/4641* (2013.01)

(58) Field of Classification Search
None
See application file for complete search history.

(56) References Cited

U.S. PATENT DOCUMENTS

| | | |
|---|---|---|
| 4,257,129 A | 3/1981 | Volz |
| 4,938,769 A | 7/1990 | Shaw |
| 5,458,637 A | 10/1995 | Hayes |
| 5,702,464 A | 12/1997 | Lackey et al. |
| 6,709,461 B2 | 3/2004 | O'Neil et al. |
| 7,105,026 B2 | 9/2006 | Johnson et al. |
| 7,309,361 B2 | 12/2007 | Wasielewski |
| 8,540,775 B2 | 9/2013 | Reich et al. |
| 8,617,250 B2 | 12/2013 | Metzger |

(Continued)

FOREIGN PATENT DOCUMENTS

| | | |
|---|---|---|
| CN | 204618488 U | 9/2015 |
| CN | 204709086 U | 10/2015 |

(Continued)

*Primary Examiner* — David H Willse
(74) *Attorney, Agent, or Firm* — Weide & Miller, Ltd.

(57) ABSTRACT

A knee replacement, a kit for a knee replacement, and a method for performing a knee replacement are provided. A tibial fixed component of the knee replacement is configured to be permanently inserted into a resected tibia of a patient. A tibial modular component of the knee replacement is removably attachable to the tibial fixed component and has an upper surface to interface with a femoral component. The tibial modular component is removable from the tibial fixed component so that in the event that the fit of the knee replacement is not correct, the tibial modular component may be replaced with a differently sized tibial modular component without removing the tibial fixed component from the bone.

16 Claims, 6 Drawing Sheets

(56) References Cited

U.S. PATENT DOCUMENTS

| | | |
|---|---|---|
| 8,632,600 B2 | 1/2014 | Zannis et al. |
| 8,728,086 B2 | 5/2014 | Smith et al. |
| 9,241,801 B1 | 1/2016 | Parry et al. |
| 9,655,750 B2 | 5/2017 | Marter |
| 2004/0225368 A1 | 11/2004 | Plumet et al. |
| 2005/0055101 A1* | 3/2005 | Sifneos .................. A61F 2/389 623/20.32 |
| 2014/0277539 A1* | 9/2014 | Cook ........................ A61F 2/30 623/20.32 |

FOREIGN PATENT DOCUMENTS

| | | | |
|---|---|---|---|
| DE | 40 11 216 C1 * | 5/1991 | ............... A61F 2/38 |
| EP | 0536457 A1 | 10/1991 | |
| EP | 0 605 337 A1 * | 7/1994 | ............... A61F 2/38 |
| EP | 0536457 B1 | 1/1997 | |
| FR | 2665073 A1 | 1/1992 | |
| FR | 2716619 | 4/1998 | |
| GB | 2307861 A | 6/1997 | |
| WO | WO2016071938 A1 | 5/2016 | |

* cited by examiner

MODULAR, PLASTIC KNEE REPLACEMENT WITH LOCKING MECHANISM

BACKGROUND

The disclosed embodiments relate to knee replacements. More specifically, the disclosed embodiments relate to all-polyethylene, modular knee replacements and methods for utilizing and implanting the same.

Conventionally, a knee joint prosthesis includes a femoral implant and a tibial implant. The femoral implant and tibial implant are designed to be surgically implanted into the distal end of the femur and the proximal end of the tibia, respectively. The femoral implant is further designed to cooperate with the tibial implant in simulating the articulating motion of an anatomical knee joint.

These femoral and tibial implants, in combination with ligaments and muscles, attempt to duplicate natural knee motion as well as absorb and control forces generated during the range of flexion.

Typical knee replacements include trial components temporarily placed in the knee prior to implantation of the permanent components to help a physician to correctly fit the knee replacement to a particular patient. During the knee replacement procedure, the physician may assemble the trial knee joint prosthesis one or more times with different trial pieces of the knee replacement that are designed to be easily removable. When the correct size and orientation of the knee replacement is identified, then a corresponding size of a permanent knee replacement is permanently implanted, such as by cementing the permanent knee replacement into a resected portion of the bone, such as the tibia or femur.

However, even when this procedure is carefully followed, a physician may still find later during the procedure that the sizing is not quite correct. However, if the permanent piece is already in place, it is difficult to remove the incorrectly sized permanent piece without removing more of the bone and increasing the risk to the patient. Thus, there is a need for an all-polyethylene, permanent knee replacement that is still easily replaceable by a physician in the event that the trial fit is insufficient.

SUMMARY

In light of the above, the disclosed embodiments provide knee replacements, knee replacement kits, and methods for performing a knee replacement. A tibial fixed component of the knee replacement is configured to be permanently inserted into a resected tibia of a patient. A tibial modular component of the knee replacement is removably attachable to the tibial fixed component and has an upper surface to interface with a femoral component. The tibial modular component is removable from the tibial fixed component so that in the event that the fit of the knee replacement is not correct, the tibial modular component may be replaced with a differently sized tibial modular component without removing the tibial fixed component from the bone.

In one embodiment, a knee replacement is provided that includes a tibial fixed component configured to be permanently inserted into a resected tibia of a patient and a tibial modular component that is removably attachable to the tibial fixed component. The tibial modular component includes an upper surface to interface with a femoral component. In some instances, the tibial fixed component is comprised completely of a polyethylene material.

The tibial fixed component may have an array of male or female connectors. The tibial modular component may have a corresponding array of female or male connectors that connect the tibial modular component to the tibial fixed component. The male or female connectors of the tibial fixed component and the female or male connectors of the tibial modular component may be cylindrical in shape, or may take on other shapes.

The tibial modular component may be selected from a plurality of tibial modular components having different sizes. In some instances, the tibial fixed component and the tibial modular component comprise a notch in a side surface configured to facilitate separation of the tibial fixed component and the tibial modular component.

In another exemplary embodiment, a modular knee replacement kit is provided and includes a tibial fixed component that is configured to be permanently inserted into a resected tibia of a patient, and a plurality of tibial modular components. The modular components are removably attachable to the tibial fixed component. Each of the plurality of tibial modular components has a different size, and each has an upper surface to interface with a femoral component.

The tibial fixed component may include a plurality of male or female connectors disposed in an array on an upper surface of the tibial fixed component. The tibial modular components may each have a corresponding plurality of female or male connectors disposed in an array on a lower surface of the tibial modular components that connect the tibial modular components to the tibial fixed component.

In some embodiments, the modular knee replacement kit may also have a plurality of trial tibial modular components that are removably attachable to the tibial fixed component. The plurality of trial tibial modular components each have a different size that corresponds to the sizes of the plurality of the tibial modular components. The plurality of trial tibial modular components may have at least one female or male connectors disposed on a lower surface of the trial tibial modular components. The female or male connectors correspond with at least one of the plurality of male or female connectors of the tibial fixed component. In some instances, the number of the female or male connectors of the trial tibial modular components is less than the number of the male or female connectors of the tibial fixed component.

The male or female connectors of the tibial fixed component, the female or male connectors of the tibial modular components, and the female or male connectors of the trial tibial modular components may be cylindrical in shape or may take on other shapes. The tibial fixed component, each of the tibial modular components, and each of the trial tibial modular components may include a notch in a side surface configured to facilitate separation of the tibial fixed component from the tibial modular components or the trial tibial modular components.

In some embodiments, the tibial fixed component comprises a keel protruding from a lower surface thereof. The keel may be formed in a tubular shape with wings on sides of the tubular shape. In other embodiments, the keel comprises a cruciform shape. An elongated stem may be provided that connects to the keel. The elongated stem and keel are configured to be inserted into a resected bone.

In another exemplary embodiment, a method for performing a knee replacement is provided. The method may include preparing a resected bone for implantation of a knee replacement, and fitting and attaching a tibial fixed component of a modular knee replacement into the resected bone. A first modular tibial component of the modular knee replacement having a first size is connected to the tibial fixed component and is checked for a proper fit. When the fit is incorrect, the first modular tibial component is removed and replaced with a second modular tibial component having a second size. The second modular tibial component is then checked to ensure a proper fit. This is done without the need to remove the tibial fixed component from the bone.

The tibial fixed component may include a plurality of male or female connectors disposed in an array on an upper surface of the tibial fixed component. Likewise, the first and second tibial modular components may include a corresponding plurality of female or male connectors disposed in an array on a lower surface of the tibial modular components. The first and second tibial modular components are connected to the tibial fixed component by interdigitating the male or female connectors of the fixed tibial component with the female or male connectors of the first and second tibial modular components.

In some embodiments, prior to connecting the first modular tibial component, the method may also include connecting a first trial tibial component from a plurality of trial tibial components having different sizes to the fixed tibial component. Each of the trial tibial components may have at least one female or male connectors corresponding to one or more of the male or female connectors of the tibial fixed component. The first trial tibial component is checked for a proper trial fit. When the trial fit is incorrect, the first trial tibial component is removed and replaced with other trial tibial components that have a different size than the first trial tibial component until a correctly sized trial tibial component having the proper trial fit is identified. The first modular tibial component is chosen with a size corresponding to a size of the correctly sized trial tibial component.

In some embodiments the tibial fixed component is fitted and attached into the resected bone via an impactor. The impactor may have at least one female or male connector corresponding with one or more of the male or female connectors of the tibial fixed component.

BRIEF DESCRIPTION OF THE DRAWINGS

The components in the figures are not necessarily to scale, emphasis instead being placed upon illustrating the principles of the invention. In the figures, like reference numerals designate corresponding parts throughout the different views.

DETAILED DESCRIPTION OF EMBODIMENTS

Figure 1:
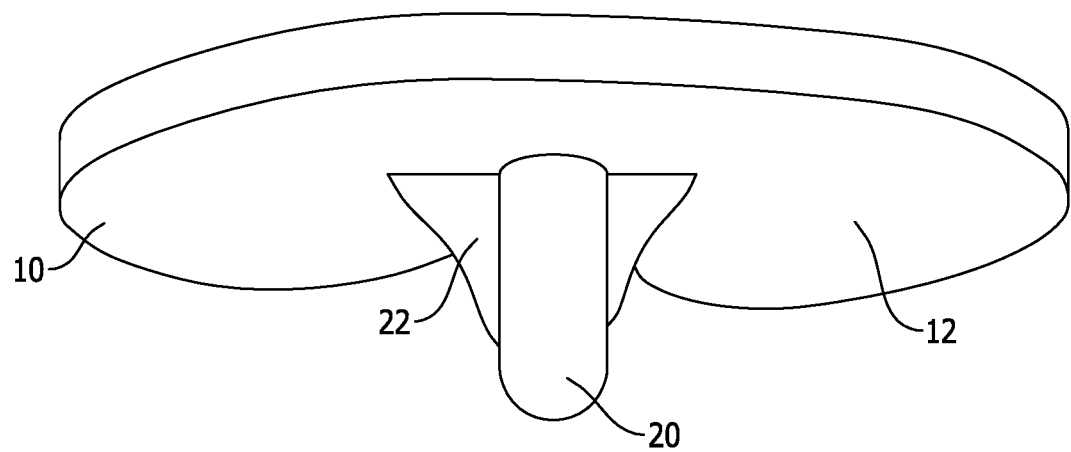
FIG. 1 shows a perspective view of a lower side of a tibial fixed component, according to one exemplary embodiment.
Figure 2:
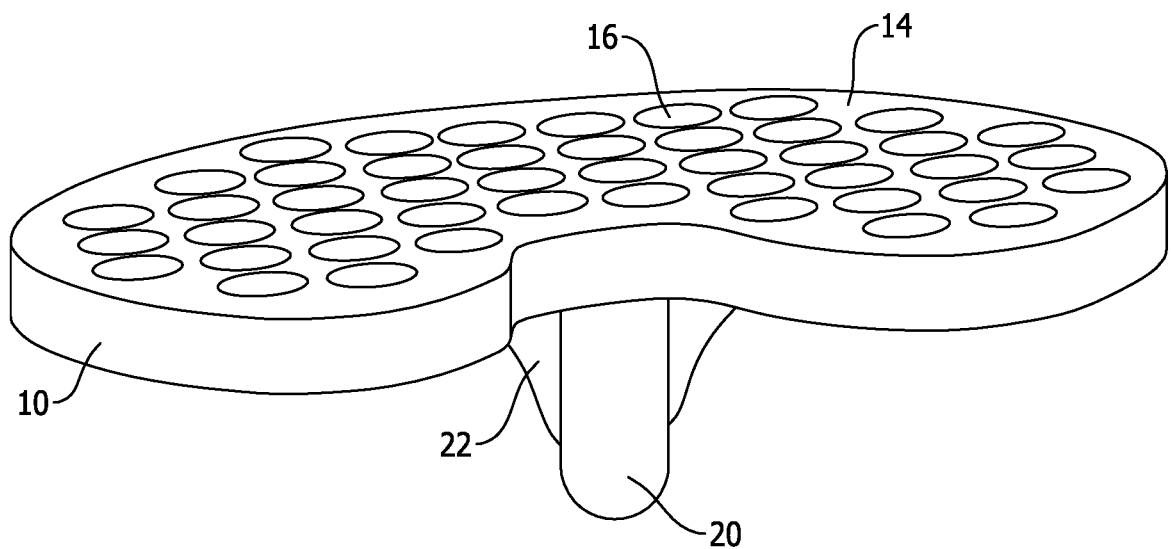
FIG. 2 shows a perspective view of an upper side of the tibial fixed component of FIG. 1.

FIG. 1 shows a perspective view of a lower side of a tibial fixed component, according to one exemplary embodiment, and FIG. 2 shows a perspective view of an upper side of the tibial fixed component of FIG. 1. A tibial fixed component 10 comprises a lower side 12 and an upper side 14. The tibial fixed component 10 is formed from a plastic, such as polyvinyl chloride (PVC), polypropylene (PP), polyethylene (PE), polystyrene (PS), nylon, polyethylene terephthalate (PET), polyimide (PA), polycarbonate (PC), acrylonitrile butadiene (ABS), polyetheretherketone (PEEK), polyurethane (PU), or the like.

A keel 20 extends from the lower side 12 of the tibial fixed component 10. The keel 20 is also formed from a plastic material. The keel 20 may be manufactured integrally with the tibial fixed component 10 or may be formed separately and may be attached to the tibial fixed component 10. For example, tibial fixed component 10 and keel 20 may be formed together injection molding or compression molding. In another example, the keel 20 is formed separate from the tibial fixed component 10 and is connected to the tibial fixed component 10 by a fastener, an adhesive, a weld, or the like.

The keel 20 may take on a variety of shapes like other keels known in the art. In FIGS. 1 and 2, the keel 20 is shown having wings 22. However, the wings 22 may be omitted. Other shapes for the keel 20 may also be possible including a cruciform shape, tubular or cylindrical shape, etc. The keel 20 may be configured to attach to other parts. For example, the wings 22 may be formed separately from the keel 20 and may fasten over the keel 20 in a modular fashion. For example, the wings 22 may be formed on a cylindrical member with internal threads that connect to external threads disposed on the outside of the keel 20.

In some embodiments, an elongated stem may attach to the keel 20 to provide further stability to the knee replacement. The elongated stem may be formed as part of the keel 20 or may attach thereto. For example, the keel 20 may have an aperture at the bottom thereof with female threads into which the elongated stem may attach. In some instances, the elongated stem may also be formed from a plastic material, such as those listed above. The stem may also include a cobalt pin to provide added support. The stem may also be formed from a metallic material and may attach to the tibial fixed component 10.

The bottom surface 12 of the tibial fixed component 10 may take on any variety of topographies as is known in the art to facilitate the interface between the tibial fixed component 10 and the bone of the patient. For example, a surface roughness may be introduced to the bottom surface 12 to facilitate adhesion of the tibial fixed component 10 to the bone with a cement. In some scenarios, augments may be added to the bottom surface 12 to compensate for any bone defects. The augments may be added to one or both the medial and lateral sides of the bottom side 12 of the tibial fixed component 10. The augments may take on any number of sizes and thickness as is needed for a given application.

A top surface 14 of the tibial fixed component 10 comprises a plurality of connectors 16. In the embodiment shown in FIG. 2, the top surface 14 of the tibial fixed component 10 has a plurality of female connectors or apertures 16 disposed throughout the top surface 14. FIG. 2 shows the plurality of female connectors 16 being arranged in rows. However, the arrangement of the female connectors 16 on the top surface 14 of the tibial fixed component 10 may be of any other suitable pattern. The connectors 16, in this embodiment, have a cylindrical shape. However, any other shape may be used for the female connectors 16 such as a triangle, square, oval, or other shape. The top surface 14 of the tibial fixed component 10 is shown to be flat, however, other topographies may also be used.

The tibial fixed component 10 is configured to be permanently implanted into a resected bone (tibia) of the patient. This maybe done in any conventional manner now known or later developed. For example, the tibial fixed component 10 may be cemented or otherwise fixed without cement into the resected tibia.

Figure 3:
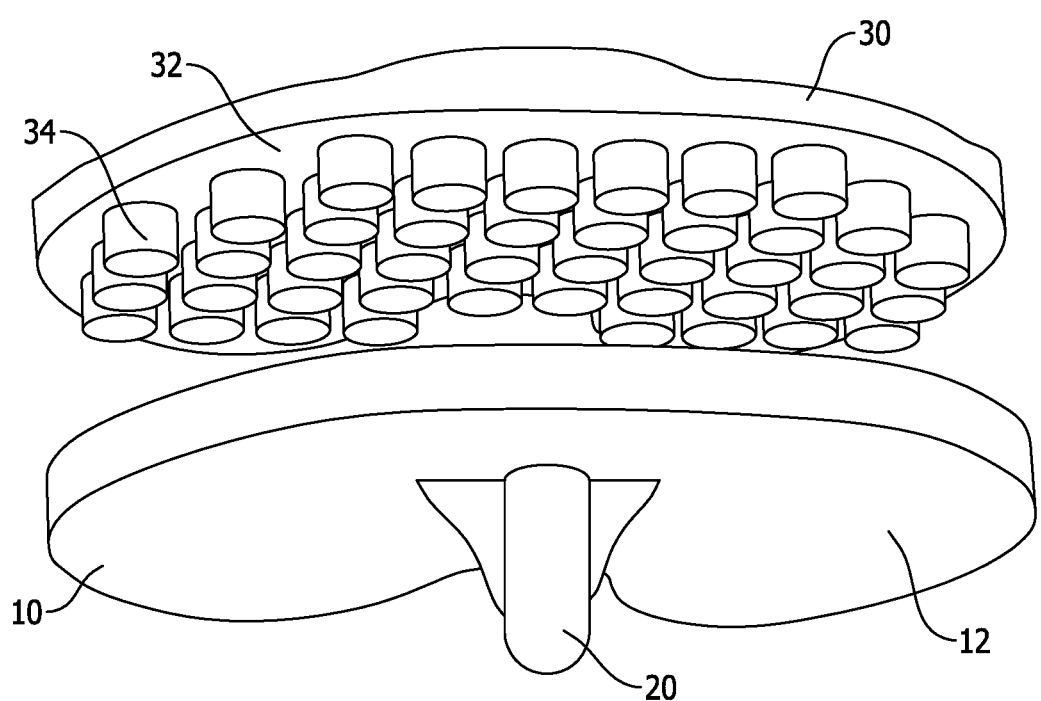
FIG. 3 shows a perspective view of the lower side of the tibial fixed component and a lower side of a tibial modular component, according to one exemplary embodiment.
Figure 4:
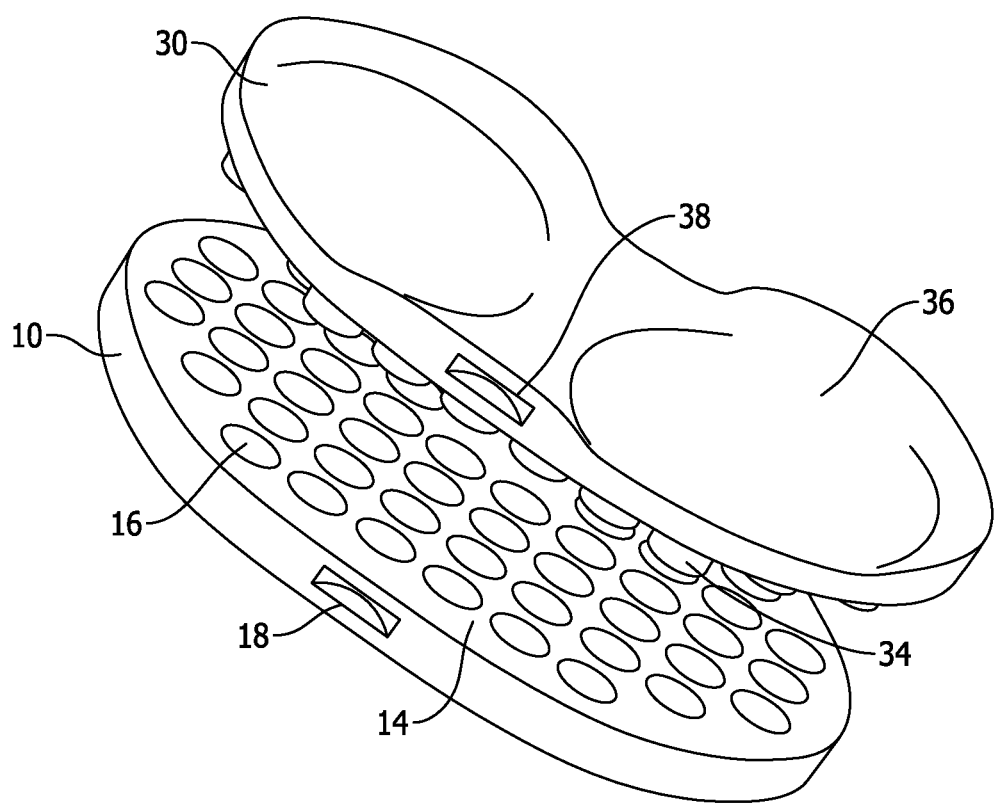
FIG. 4 shows a perspective view of the upper side of the tibial fixed component and an upper side of the tibial modular component, according to one exemplary embodiment.

The female connectors 16 of the tibial fixed component 10 are configured to interdigitate and fasten with connectors of a tibial modular component 30. FIG. 3 shows a perspective view of the lower side of the tibial fixed component and a lower side of a tibial modular component, and FIG. 4 shows a perspective view of the upper side of the tibial fixed component and an upper side of the tibial modular component, according to one exemplary embodiment. In FIGS. 3 and 4, a tibial modular component 30 comprises a lower surface 32 with a plurality of male connectors 34. As shown in FIG. 4, the male connectors 34 are configured to correspond with the female connectors 16 on the tibial fixed component 10.

The male connectors 34 are shown to have a cylindrical shape However, the male connectors 34 may take on any other shape such as a triangle, square, oval, etc. The male connectors 34 may also be disposed in any suitable arrangement corresponding to the female connectors 16 of the tibial fixed component 10. The male connectors 34 are configured to interdigitate with the female connectors 16 to affix the tibial modular component 30 to the tibial fixed component 10. To establish a secure fit between the male connectors 34 and the female connectors 16, the sizes of the connectors 34, 16 may be such to create an interference fit between the connectors 34, 16. In some embodiments, a taper such as a Morse taper may be added to the connectors 34, 16 such that the connectors 34, 16 securely interface and lock together.

The tibial modular component 30 is provided in several sizes in both trial and definitive forms. For example, to create an appropriate fit, the tibial modular component 30 may have a thickness ranging from 8 mm to 26 mm. Trial tibial modular components 30 may be configured to be easily removable from the tibial fixed component 10. For example, the trial tibial modular components 30 may not include all corresponding male connectors 34 of the female connectors 16 of the tibial fixed component 10. Further, the male connectors 34 may be sized so that they do not lock into the female connectors 16 of the tibial fixed component 10.

The definitive tibial modular components 30 are configured to securely attach to the tibial fixed component 10 to provide a stable replacement joint for the patient. Accordingly, in some instances, one or more of the male connectors 34 may be provided with an annular flange surrounding the male connector 34 and that fits into a corresponding groove formed into the female connectors 16. Similarly, a spring-loaded ring may be disposed in a groove on the outside of one or more of the male connectors 34 that is configured to expand into a corresponding groove formed into the female connectors 16. Other similar mechanisms may also be used to secure the connection between the tibial fixed component 10 and the tibial modular component 30.

Figure 5:
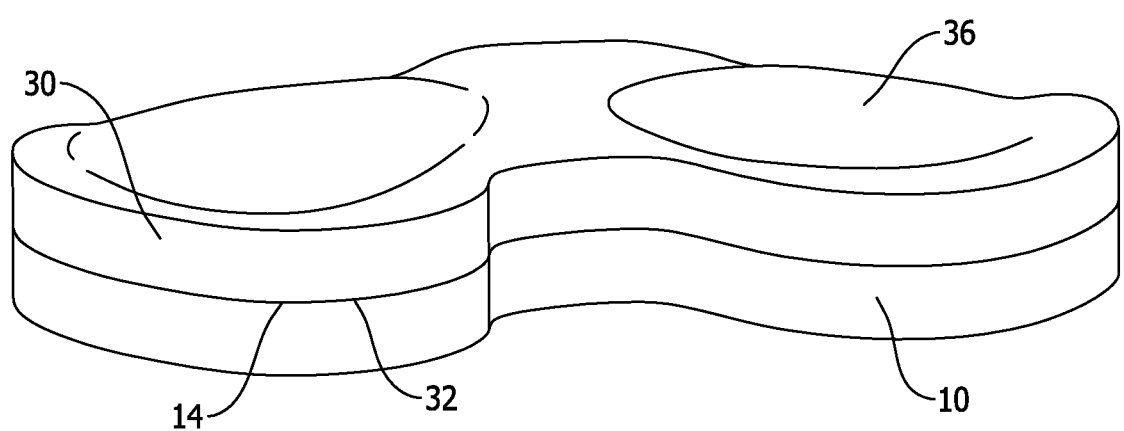
FIG. 5 shows a perspective view of the tibial fixed component and the tibial modular component in an assembled state, according to an exemplary embodiment.

FIG. 5 shows a perspective view of the tibial fixed component and the tibial modular component in an assembled state, according to an exemplary embodiment. When the male connectors 34 are inserted into the female connectors 16, the lower surface 32 of the tibial modular component 30 comes into contact with the top surface 14 of the tibial fixed component 10 forming a secure, stable connection between the two.

The shape and topography of the upper surface 36 of the tibial modular component 30 may be formed in any variety of shapes to conform to several different known knee replacements depending on the type of femoral component being used. For example, the upper surface 36 of the tibial modular component 30 may be formed to facilitate any of the following types of knee replacements including medial pivot, cruciate retaining, cruciate sacrificing, cruciate substituting, cam and post, hinge, and mobile bearing.

The tibial modular component 30 may be formed from a plastic, such as those listed above, similar to the tibial fixed component 10. In some instances, however, some or all of the tibial modular component 30 may be formed from a metal, depending on the femoral component being used. It also should be noted that while the tibial modular component 30 is shown herein as comprising male connectors 34 and the tibial fixed component 10 is shown herein as comprising female connectors 16, the tibial modular component 30 may instead comprise the female connectors 16 and the tibial fixed component 10 may comprise the male connectors 34. In other embodiments, each of the tibial fixed component 10 and the tibial modular component 30 may comprise some male and female connectors.

With the connection of the tibial modular component 30 to the tibial fixed component 10 as shown in FIG. 5, a stable and secure tibial component can be created for a patient. However, in the event that the combination of the tibial fixed component 10 and the tibial modular component 30 together were not sized correctly for the patient, even when testing with a trial tibial modular component 30, the physician may be able to quickly and easily replace the tibial modular component 30 without significant added time or trauma to the patient.

Because the tibial component is separated into the tibial fixed component 10 and the tibial modular component 30, the tibial modular component 30 may be removed from the tibial fixed component 10. The connectors 16, 34 are configured to not only provide a stable connection between the tibial fixed component 10 and the tibial modular component 30, but also to facilitate removal of the tibial modular component 30 from the tibial fixed component 10. When a physician applies sufficient force to separate the tibial modular component 30 from the tibial fixed component 10, the connectors 16, 34

The removal of the tibial modular component 30 from the tibial fixed component 10 may be facilitated by a tool. In the embodiment shown in FIG. 4, the tibial fixed component 10 includes a notch or indentation 18. Similarly, the tibial modular component 30 includes a corresponding notch or indentation 38. A tool may be used to apply forces in opposite directions at each of the notches 18, 38 to separate the tibial modular component 30 from the tibial fixed component 10. While the notches 18, 38 are shown disposed at a central location along the sides of each of the tibial fixed component 10 and the tibial modular component 30, this is only exemplary and the notches 18, 38 may be placed at any suitable corresponding locations on the tibial fixed component 10 and the tibial modular component 30. Further, there may be multiple notches 18, 38 on each of the tibial fixed component 10 and tibial modular component 30 to facilitate separation.

Figure 6:
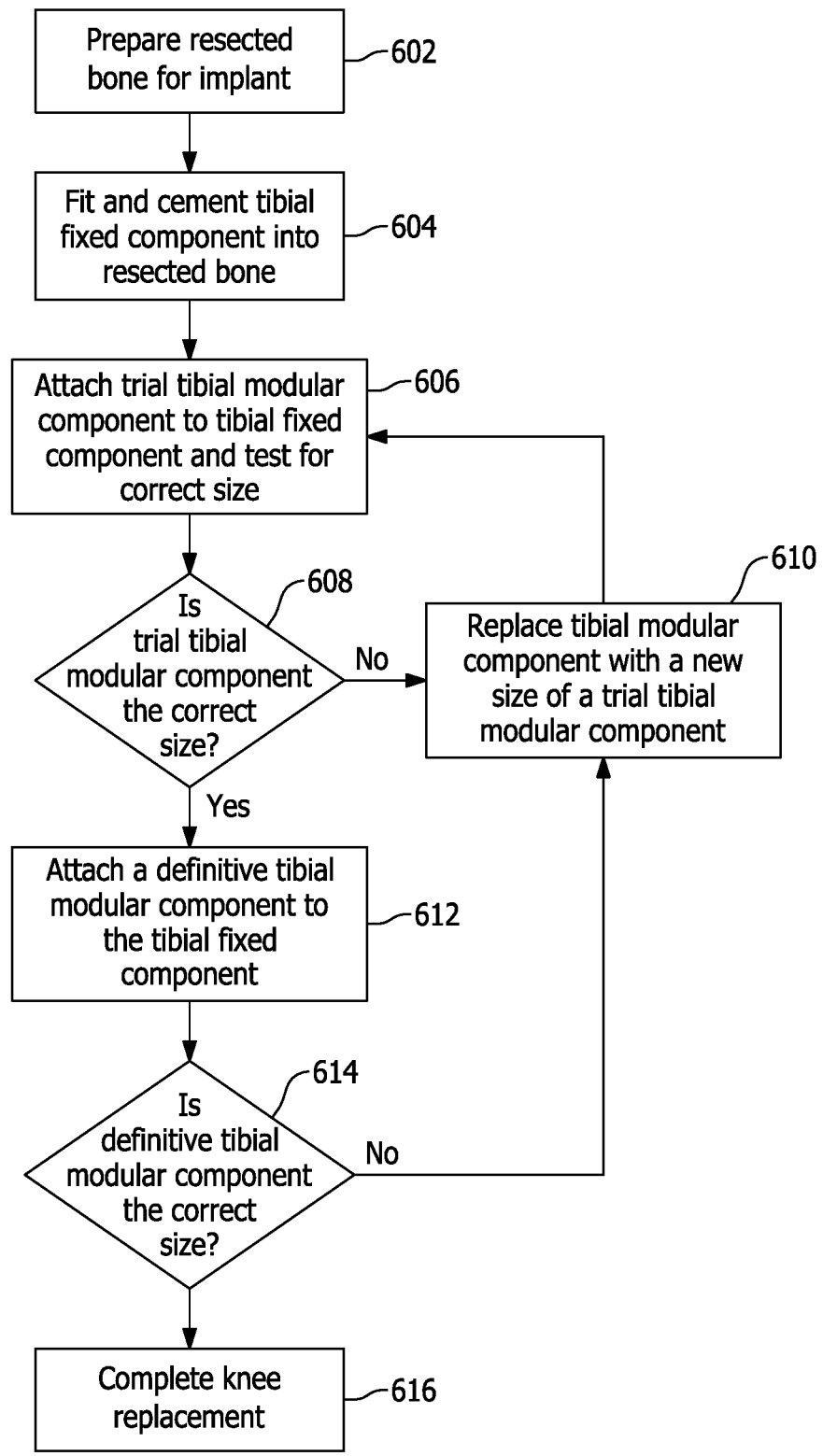
FIG. 6 shows a method of utilizing a modular all-poly knee replacement, according to one exemplary embodiment.

FIG. 6 shows a method of utilizing a modular all-poly knee replacement, according to one exemplary embodiment. In step 602, the physician prepares the bone (tibia) for the knee replacement. This may include removing material to create a recess that corresponds with the keel 20 of the tibial fixed component 10, for example. Next, the tibial fixed component 10 is fit and cemented into place in the resected bone, as shown in step 604. The physician may use an impactor to help set the tibial fixed component 10 into position. In this instance, an impactor may be manufactured with connectors that fit into the female connectors 16 of the tibial fixed component 10. The impactor may be hit with a mallet or other tool to seat the tibial fixed component 10 into the resected bone.

With the tibial fixed component 10 in position, the physician may attach a trial tibial modular component 30 to the tibial fixed component 10 and test for the correct size. As mentioned above, the tibial modular component 30 may be produced in several sizes in both trial and definitive form. The trial forms of the tibial modular components 30 may be built with fewer or smaller connectors than that shown in the Figures to facilitate easy removal. In step 608, the physician determines whether the trial tibial modular component 30 is the correct size. If not, the method proceeds to step 610.

In step 610, the physician removes the tibial modular component 30 to replace it with a different size to find the correct size of the tibial modular component 30 to be used. For example, if the previous sized tibial modular component 30 was too small, the physician may choose a larger trial tibial modular component 30 with which to proceed. The method then returns to step 606 where the physician attaches and sizes the new trial tibial modular component 30. This process is repeated until the physician finds the right sized trial tibial modular component 30 in step 608.

When a correct size of the tibial modular component 30 is found using the trial tibial modular components 30 in step 608, the method proceeds to step 612. In step 612, the physician attaches the definitive tibial modular component 30 to the tibial fixed component 10. The physician chooses the size of the definitive tibial modular component 30 based on the correctly sized trial tibial modular component 30 from step 608. The definitive tibial modular component 30 is attached to the tibial fixed component 10 via the interdigitating male and female connectors 16, 34 as described above.

In step 614, the physician again tests the fit of the tibial component of the knee replacement which is now comprised of the tibial fixed component 10 and the definitive tibial modular component 30. If, even after sizing the tibial modular component 30 with the trial tibial modular components 30, the physician finds that the size of the definitive modular component 30 is not correct, the method may again return to step 610 where the tibial modular component 30 is removed (the definitive tibial modular component 30 in this instance) and a new trial tibial modular component 30 is sized. The definitive tibial modular component 30 may be removed with the aid of a tool and notches 18, 38 formed in the tibial fixed component 10 and definitive modular component 30, as described above. In this manner, even if the definitive tibial modular component 30 is found to be incorrectly sized, the physician can easily and safely correct the size without significantly added time and trauma resulting from the procedure.

Once it is affirmed that the correct definitive tibial modular component 30 is in place, the physician may complete the knee replacement procedure, as is now known or will be later developed in step 616.

Figure 7A:
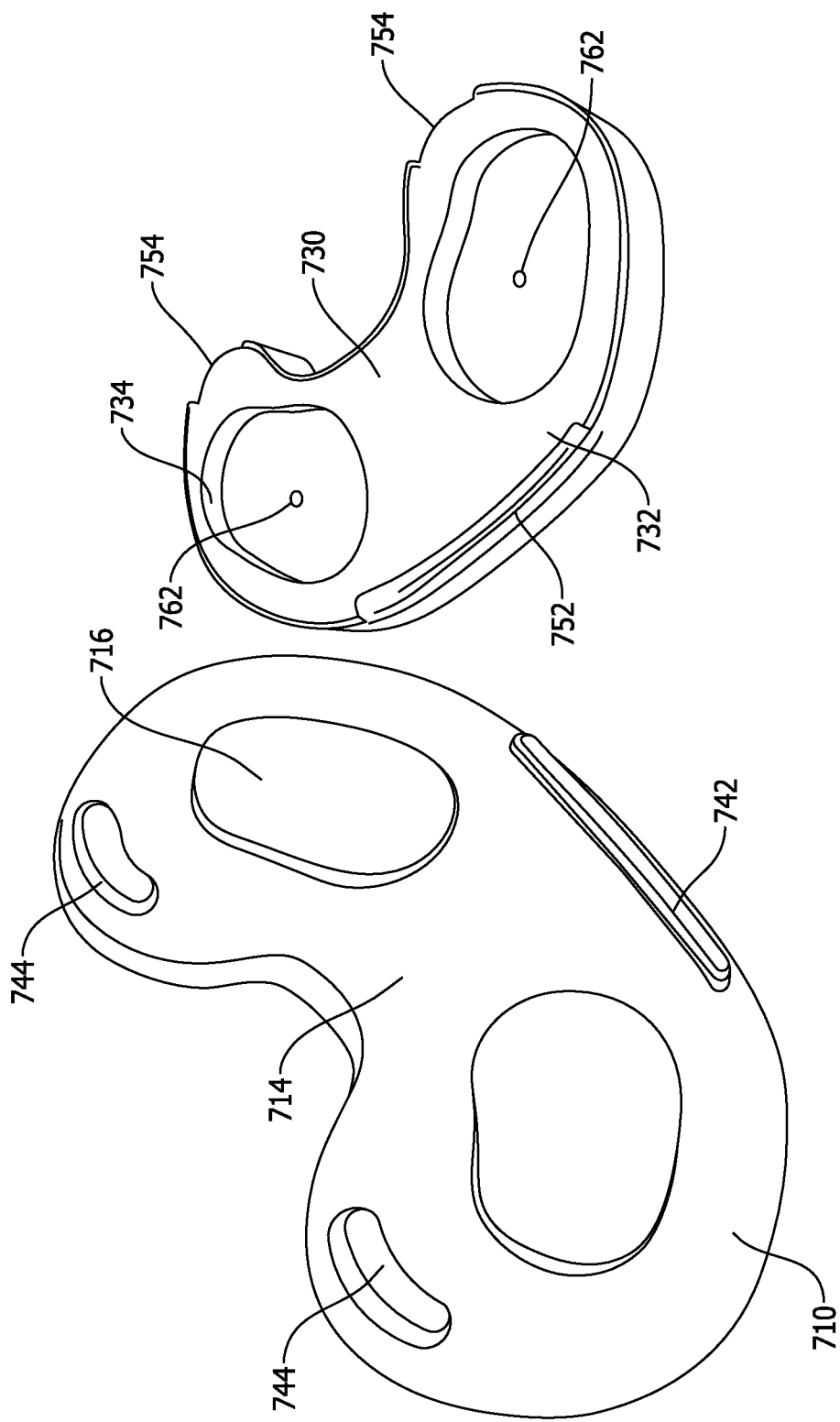
FIG. 7A shows a tibial fixed component and a tibial modular component according to another exemplary embodiment.
Figure 7B:
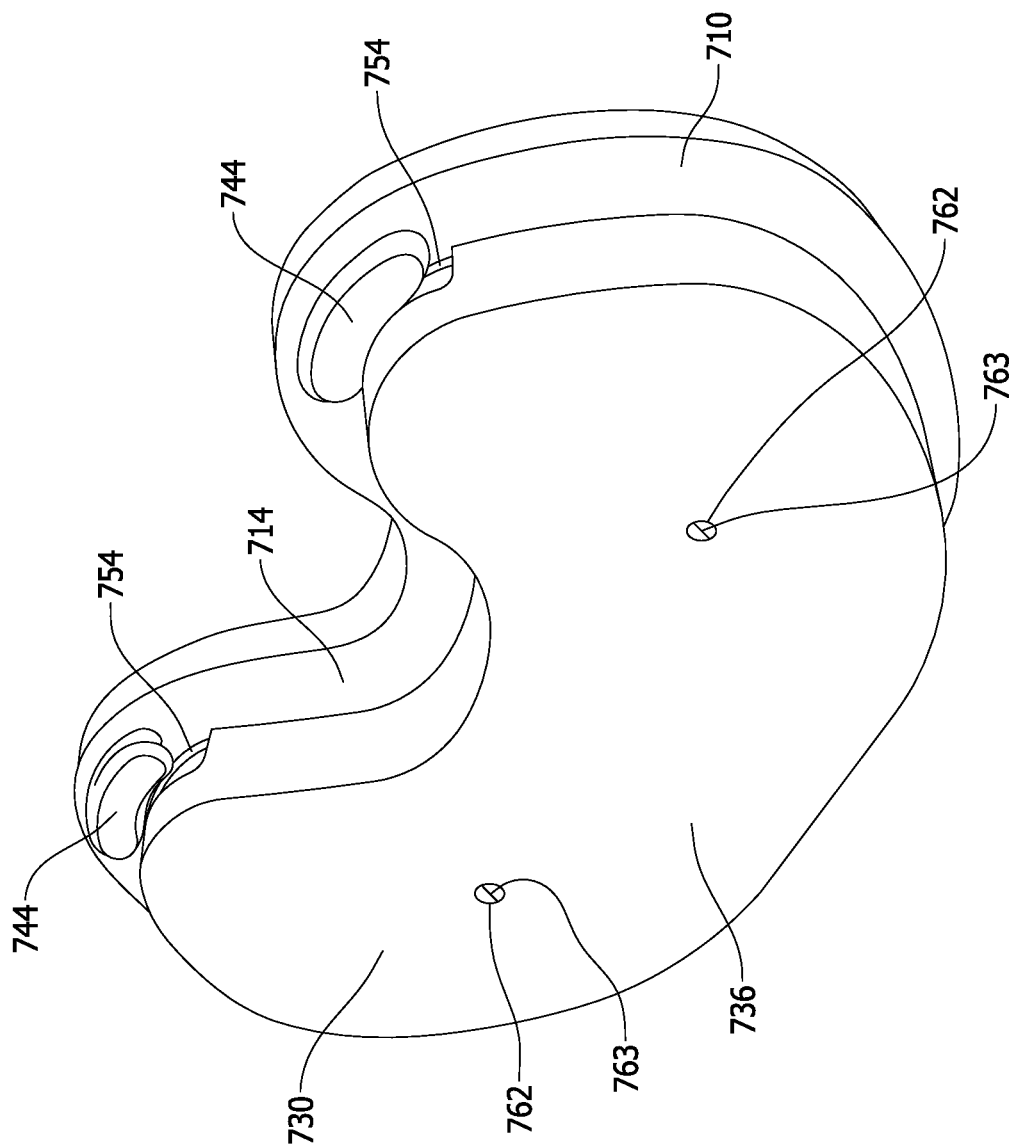
FIG. 7B shows an assembled view of the tibial fixed component and tibial modular component shown in FIG. 7A.

FIG. 7A shows a tibial fixed component and a tibial modular component according to another exemplary embodiment, and FIG. 7B shows an assembled view of the tibial fixed component and tibial modular component shown in FIG. 7A. As shown in FIG. 7A, a tibial fixed component 710 comprises connectors 716 extending from the upper surface 714. Unlike the connectors 14, in this embodiment the connectors 716 are male connectors and are not cylindrical in shape. However, it is noted that the connectors 716 may also be cylindrical or take on a variety of other shapes as desired.

A tibial modular component 730 is also provided that includes connectors 734 on a lower surface 732. The connectors 734 are female connectors that are shaped and sized to correspond with connectors 716 of the tibial fixed component 710. The tibial fixed connectors 716 and tibial modular connectors 734 are sized to have a tight, interference type fit so that the tibial modular component 730 can be fixed to the tibial fixed component 710 without the need for adhesives or separate fasteners.

To further aid in the connection between the tibial fixed component 710 and the tibial modular component, a front tab 742 and rear tabs 744 are provided on the upper surface 714 of the tibial fixed component. The tibial modular component 730 is sized to fit within the front tab 742 and rear tabs 744. The tibial modular component 730 comprises a front notch 752 that corresponds to the front tab 742 of the tibial fixed component 710. The tibial modular component also comprises rear notches 754 that correspond to the rear tabs 744. The notches 752, 754 are formed in side surfaces of the tibial modular component 730 extending from the lower surface 732 of the tibial modular component 730 to correspond to the tabs 742, 744.

The tabs 742, 744 may be formed of any suitable material. For example, the tabs 742, 744 may be formed integrally with the tibial base component 710 and may thus be formed from a plastic material such as those listed above. In other embodiments, the tabs may be embedded into the tibial fixed component 710 and may be formed of a plastic or metallic material. In other embodiments, the tabs 742, 744 may be attached to the tibial fixed component 710 via a fastener or an adhesive.

When the tibial modular component 710 is attached to the tibial fixed component 730 as shown in FIG. 7B, the connectors 734 of the tibial modular component 730 fit over and attach to the connectors 716 of the tibial fixed component 710 to lock the tibial modular component 730 to the tibial fixed component 710. Further the tabs 742, 744 of the tibial fixed component 710 snap or fit over/into the notches 752, 754 of the tibial modular component 710, further strengthening the connection between the tibial fixed component 710 and the tibial modular component 730.

In this embodiment, as before, even though the connection is secure for a permanent knee replacement, the tibial modular component 730 is still selectively removable and reattachable to the tibial fixed component 710. This allows a physician to make corrections even if a definitive tibial modular component 730 is attached to the tibial fixed component.

As also shown in FIGS. 7A and 7B, the tibial modular component 762 comprises through holes 762. The through holes 762 are disposed in the connectors 734 and extend through to the upper surface 736 of the tibial modular component 730. The through holes facilitate attachment and detachment of the tibial modular component 730 from the tibial fixed component 710. Due to the tight fit of the connectors 716, 734, it may be difficult to detach the tibial modular component 730 from the tibial fixed component 710. This is not only because of the physical interaction between the connectors 716, 734, but also due to a vacuum effect created as the connectors 716, 734 are forced apart before air can easily enter the space created between the connectors 716, 734. With the through holes 762, the vacuum effect is eliminated, and a physician can more easily attach and detach the tibial modular component 730 from the tibial fixed component.

In some embodiments, the holes 762 may comprise valves 763 such as one way valves 763 that only allow air to pass in a single direction. In some embodiments, there may be multiple holes 762 in a single connector 734. The holes 762 may have different one way valves 763 to facilitate air passing through one hole 762 when the connectors 716, 734 are connected and through another hole 762 when the connectors 716, 734 are detached.

While various embodiments of the invention have been described, it will be apparent to those of ordinary skill in the art that many more embodiments and implementations are possible that are within the scope of this invention. In addition, the various features, elements, and embodiments described herein may be claimed or combined in any combination or arrangement.

What is claimed is:

1. A knee replacement comprising:
    a tibial fixed component comprised of a plastic material and configured to be permanently inserted into a resected tibia of a patient, the tibial fixed component having an upper surface, the upper surface comprising:
        a plurality of male or female connectors,
        a front tab disposed proximate to an edge of the upper surface, and
        a rear tab disposed proximate to an edge of the upper surface; and
    a tibial modular component that is selectively attachable and detachable to the tibial fixed component, the tibial modular component comprising
        a lower surface configured to interface with the upper surface of the tibial fixed component, the lower surface comprising a plurality of female or male connectors corresponding to the male and female connectors of the tibial fixed component, the female or male connectors of the tibial modular component comprising through holes extending from the lower surface of the tibial modular component to an upper surface of the tibial modular component, the through holes comprising air valves to facilitate air passage when the female or male connectors of the tibial modular component connect with and/or detach from the male and female connectors of the tibial fixed component;
        notches disposed in side surfaces of the tibial modular component, the notches corresponding to the front tab and the rear tab of the tibial fixed component, and
        the upper surface to interface with a femoral component.

2. The knee replacement of claim 1, wherein the male or female connectors of the tibial fixed component and the female or male connectors of the tibial modular component are cylindrical in shape.

3. The knee replacement of claim 1, wherein the tibial modular component is selected from a plurality of tibial modular components having different sizes.

4. The knee replacement of claim 1, wherein the tibial fixed component and the tibial modular component comprise a separation notch in a side surface configured to facilitate separation of the tibial fixed component and the tibial modular component.

5. A modular knee replacement kit comprising:
    a tibial fixed component comprised of a plastic material and configured to be permanently inserted into a resected tibia of a patient, the tibial fixed component having an upper surface, the upper surface comprising:
        a plurality of male or female connectors,
        a front tab disposed proximate to an edge of the upper surface, and
        a rear tab disposed proximate to an edge of the upper surface; and
    a plurality of tibial modular components that are selectively attachable and detachable to the tibial fixed component, the plurality of tibial modular components each having a different size and each comprising:
        a lower surface configured to interface with the upper surface of the tibial fixed component, the lower surface comprising a plurality of female or male connectors corresponding to the male and female connectors of the tibial fixed component, the female or male connectors of the tibial modular component comprising through holes extending from the lower surface of the tibial modular component to an upper surface of the tibial modular component, the through holes comprising air valves to facilitate air passage when the female or male connectors of the tibial modular component connect with and/or detach from the male and female connectors of the tibial fixed component;
        notches disposed in side surfaces of the tibial modular component, the notches corresponding to the front tab and the rear tab of the tibial fixed component, and
        the upper surface to interface with a femoral component.

6. The modular knee replacement kit of claim 5, further comprising a plurality of trial tibial modular components that are removably attachable to the tibial fixed component, the plurality of trial tibial modular components each having a different size corresponding to the sizes of the plurality of the tibial modular components.

7. The modular knee replacement kit of claim 6, wherein each of the plurality of trial tibial modular components comprises at least one female or male connectors disposed on a lower surface of the trial tibial modular components, the at least one female or male connectors corresponding with at least one of the plurality of male or female connectors of the tibial fixed component, and wherein a number of the at least one female or male connectors of the trial tibial modular components is less than a number of the male or female connectors of the tibial fixed component.

8. The modular knee replacement kit of claim 7, wherein the male or female connectors of the tibial fixed component, the female or male connectors of the tibial modular components, and the at least one female or male connectors of the trial tibial modular components are cylindrical in shape.

9. The modular knee replacement kit of claim 7, wherein the tibial fixed component, each of the tibial modular components, and each of the trial tibial modular components comprise a separation notch in a side surface configured to facilitate separation of the tibial fixed component and the tibial modular components or the trial tibial modular components.

10. The modular knee replacement kit of claim 5, wherein the tibial fixed component comprises a keel protruding from a lower surface thereof.

11. The modular knee replacement kit of claim 10, wherein the keel comprises a tubular shape and wings on sides of the tubular shape.

12. The modular knee replacement kit of claim 10, wherein the keel comprises a cruciform shape.

13. The modular knee replacement kit of claim 10, further comprising an elongated stem that connects to the keel, the elongated stem and keel being configured to be inserted into a resected bone.

14. A knee replacement comprising:
a tibial fixed component comprised of a plastic material and configured to be permanently inserted into a resected tibia of a patient, the tibial fixed component having an upper surface, the upper surface comprising a plurality of male or female connectors;
a tibial modular component that is selectively attachable and detachable to the tibial fixed component, the tibial modular component comprising
 a lower surface configured to interface with the upper surface of the tibial fixed component, the lower surface comprising a plurality of female or male connectors corresponding to the male and female connectors of the tibial fixed component,
 an upper surface to interface with a femoral component, and
 through holes disposed in the female or male connectors of the lower surface of the tibial modular component, the through holes extending from the lower surface of the tibial modular component to the upper surface of the tibial modular component, the through holes comprising air valves to facilitate air passage when the female or male connectors of the tibial modular component connect with and/or detach from the male and female connectors of the tibial fixed component.

15. The knee replacement of claim 14, wherein the tibial fixed component further comprises a front tab disposed proximate to an edge of the upper surface and a rear tab disposed proximate to an edge of the upper surface, and the tibial modular component comprises notches disposed in side surfaces of the tibial modular component, the notches corresponding to the front tab and the rear tab of the tibial fixed component.

16. The knee replacement of claim 14, wherein the male or female connectors of the tibial fixed component and the female or male connectors of the tibial modular component are cylindrical in shape.

\* \* \* \* \*